United States Patent [19]
Aretz et al.

[11] Patent Number: 4,745,061
[45] Date of Patent: May 17, 1988

[54] NOVEL D-AMINOACID TRANSAMINASE AND ITS USE

[75] Inventors: Werner Aretz, Kelkheim; Klaus Sauber, Schwalbach, both of Fed. Rep. of Germany

[73] Assignee: Hoechst Aktiengesellschaft, Fed. Rep. of Germany

[21] Appl. No.: 811,466

[22] Filed: Dec. 20, 1985

[30] Foreign Application Priority Data

Dec. 22, 1984 [DE] Fed. Rep. of Germany ....... 3447023

[51] Int. Cl.$^4$ .......................... C12N 9/10; C12N 9/06; C12Q 1/52; C12P 35/00; C12P 13/04; C12P 7/50; C07B 19/02; C12R 1/10
[52] U.S. Cl. ...................... 435/193; 435/16; 435/47; 435/106; 435/143; 435/191; 435/280; 435/836
[58] Field of Search .............. 435/193, 191, 47, 106, 435/280, 143

[56] References Cited

U.S. PATENT DOCUMENTS 3,801,458  4/1974  Fildes et al. .......................... 435/47

FOREIGN PATENT DOCUMENTS 3333453  9/1983  Fed. Rep. of Germany .

Primary Examiner—Lionel M. Shapiro
Attorney, Agent, or Firm—Finnegan, Henderson, Farabow, Garrett & Dunner

[57] ABSTRACT

A D-aminoacid transaminase which converts CPC with Δ-keto acids into Δ-ketoadipinyl-7-ACA can be isolated from *Bacillus Licheniformis* ATCC 9945. This transamination can be applied to other D-amino acids and can also be used for the preparation of D-amino acids from Δ-keto acids. The enzyme is also suitable for resolving racemates of D,L-amino acids and for detection of Δ-keto acids alongside L-amino acids.

3 Claims, No Drawings

NOVEL D-AMINOACID TRANSAMINASE AND ITS USE

Cephalosporin C (CPC) is converted into 7-aminocephalosporanic acid (7-ACA) industrially via the α-ketoadipinyl compound stage. German Offenlegungsschrift No. 2,219,454 describes a process in which this step is effected with activated cells of *Trigonopsis variabilis* under aerobic conditions. This step is oxidative deamination, in which hydrogen peroxide is formed as a by-product. However, the active enzyme from this yeast, D-aminoacid oxidase, is sensitive towards hydrogen peroxide, which means that multiple use of the enzyme is limited.

In contrast, the invention relates to a novel D-aminoacid transaminase which converts CPC with α-keto acids into α-ketoadipinyl-7-ACA and the corresponding D-α-amino acid. This conversion is thus a transamination, the amino group of CPC being converted non-oxidatively into the keto group, which is also why no hydrogen peroxide is released.

The enzyme according to the invention is formed by the bacterial strain *Bacillus licheniformis* ATCC 9945 and can be isolated from the cells after disruption in a manner which is known per se, the conversion of CPC with α-keto acids into α-ketoadipinyl-7-ACA being a possible criterion for discovering the fraction in which the enzyme according to the invention is to be found. It should be taken into consideration here that the strain mentioned forms another D-aminoacid transaminase which, however, is not capable of converting CPC.

However, the capacity of the enzyme according to the invention is not restricted to this conversion of CPC into α-ketoadipinyl-7-ACA, but it can quite generally transaminate D-α-amino acids with α-keto acids:

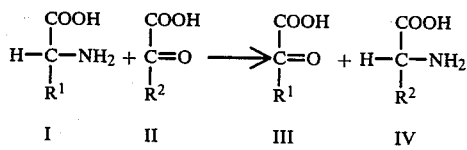

$$\begin{array}{cccc} \text{COOH} & \text{COOH} & \text{COOH} & \text{COOH} \\ | & | & | & | \\ \text{H}-\text{C}-\text{NH}_2 + & \text{C}=\text{O} & \longrightarrow \text{C}=\text{O} + \text{H}-\text{C}-\text{NH}_2 \\ | & | & | & | \\ \text{R}^1 & \text{R}^2 & \text{R}^1 & \text{R}^2 \\ \text{I} & \text{II} & \text{III} & \text{IV} \end{array}$$

α-Keto acids (or salts thereof) of the general formula II which are advantageously employed are readily accessible compounds, such as pyruvic acid, oxaloacetic acid, phenylpyruvic acid, α-ketoglutaric acid or α-ketoadipic acid.

As can already be seen from the conversion of CPC, the radical $R^1$ is fairly uncritical in the D-α-amino acids of the general formula I. The customary amino acids as well as dipeptides, for example, can therefore be employed.

The invention accordingly relates to the use of the novel enzyme for conversion of D-α-amino acids into the corresponding α-keto acids, and also for the preparation of D-amino acids from α-keto acids. According to the invention, the novel enzyme can thus also be used for resolving racemates of D,L-amino acids, since the L-amino acid is not thereby attacked, but the D-amino acid is converted into the corresponding α-keto acid, which can easily be separated off. An α-keto acid which leads to a D-α-amino acid which can easily be separated from the desired L-amino acid out of the reaction mixture is advantageously chosen for this reaction.

In an embodiment of the last process mentioned, the L-amino acid from the racemate can likewise be converted into the α-keto acid with the aid of an L-aminoacid oxidase. The enzymes and process from German Patent Application No. P 33 33 453.6 are preferably suitable for this.

The enzyme according to the invention is furthermore suitable for the detection of α-keto acids alongside L-amino acids, in particular on the micro scale.

The strain *Bacillus Licheniformis* ATCC 9945 is generally accessible. It was originally described as *Bacillus subtilis* (C. B. Thome, J. Bacteriology 69 (1955) 357–362). A preferred process for the fermentation of this strain comprises fermenting it under submerged conditions in a nutrient medium containing 0.1 to 1% of carbohydrates, 1 to 5% of organic nitrogen compounds and an inducer, preferably an amino acid in a concentration of 0.1 to 1%, in particular D,L-glutamic acid. The fermentation is advantageously carried out at 25° to 35° C., in particular at about 30° C., until the stationary phase is reached, which is the case after about 24 hours.

After harvesting the cells, these are disrupted, which can be effected mechanically or enzymatically. Mechanical disruption is carried out in a known manner, for example by ultrasound, a French press or a ®DYNO-Mill (Willi Bachofen, Basle), but disruption is preferably enzymatic, by treatment with lysozyme.

The supernatant is subjected to fractionated ammonium sulfate precipitation with subsequent dialysis, and the dialysis residue if further purified via ion exchange chromatography. Esterases and β-lactamases are thereby removed and the D-transaminases are split into fractions. The enzyme according to the invention is obtained as the second transaminase-active fraction using a high-resolution diethylaminoethyl-modified agarose.

The invention is illustrated in more detail in the following examples. Unless indicated otherwise, percentages relate to the weight.

EXAMPLE 1

The strain *Bacillus licheniformis* ATCC 9945 is kept on slant tubes with the following composition:
 0.3% of Bacto beef extract
 0.5% of Bacto peptone
 1.5% of agar
 (pH 7.0)

After an incubation period of 2–3 days at 30° C., the spores are suspended with 10 ml of physiological saline solution and 1 ml of this suspension is used for inoculating 100 ml of preculture of the following composition:
 1% of yeast extract
 0.8% of nutrient broth
 0.5% of maltose
 (pH 7.5)

The flask is incubated at 190 rpm on rotary shaker at 30° C. for 24 hours. 50 ml of this preculture are then introduced into conical flasks of 2 liters capacity containing in each case 500 ml of nutrient solution of the following composition, and the mixture is shaken as the main culture at 30° C. and 190 rpm for 24 hours:
 Main culture medium:
 1% of yeast extract
 0.8% of nutrient broth
 0.5% of D,L-glutamic acid
 (pH 7.2)

The D-aminoacid transaminase (DATA) activity reaches its maximum in the stationary growth phase at 0.5 units/g of cells.

EXAMPLE 2

Bacillus licheniformis ATCC 9945 is cultured in a preculture (500 ml) as described in Example 1 and, after 24 hours, inoculated into a 12-liter fermenter containing 9 liters of the abovementioned main culture nutrient medium. The fermentation time is 22–26 hours at 30° C., at a rate of aeration of 0.15 vvm and at 300 rpm. The DATA activity corresponds to that in Example 1.

EXAMPLE 3

The cell disruption necessary for isolation of the DATA is effected by an enzymatic route. For this, the cells are taken up (0.5 g/ml) in K phosphate buffer (pH 7.0, 10 mM+10 μM pyridoxal phosphate), 1 mg of lysozyme/ml of cell suspension is added and the mixture is incubated at 190 rpm and 30° C. for 10–30 minutes. After a microscopic check, the incubation batch is centrifuged and the supernatant is further processed as the crude extract.

EXAMPLE 4

The crude extract obtained according to Example 3 is subjected to fractionated ammonium sulfate precipitation:

Ammonium sulfate is added to 208 ml of the crude extract to 30% saturation and the mixture is centrifuged. Further ammonium sulfate is added to the supernatant to 60% saturation and the mixture is centrifuged. The precipitate is taken up in 22 ml of phosphate buffer (10 mM, pH 8.0) containing 10 μM pyridoxal phosphate and the mixture is dialyzed against the same buffer overnight.

EXAMPLE 5

15 ml of an enzyme extract prepared according to Example 4 are introduced onto a column (total volume 100 ml) containing a diethylaminoethyl-modified agarose (DEAE-sepharose ® FF from Pharmacia), which has first been equilibrated with 10 mM potassium phosphate buffer (pH 8.0). The column is eluted at pH 8.0 with a gradient of 0.15 to 0.5 M NaCl in the starting buffer. Two activities are eluted (tested with D-Ala). Only the second activity, eluted at about 230 mM NaCl, is CPC-active. This fraction contains less than 1% esterase activity in comparison with the starting material.

EXAMPLE 6

The D-transaminase-active fractions obtained according to Example 5 are combined. α-Ketoadipinyl-7-ACA is formed by incubation (at 37° C.) of CPC (20 mM) and α-keto-glutarate (20 mM), in phosphate buffer (50 mM, pH 8.0), with the fraction eluted at about 230 mM NaCl.

Separation can be effected by HPLC on "reversed phase" material (RP-18 silica gel, modified with octadecyl radicals, mobile phase: 3% of methanol) (UV detection).

The following table shows further reactions with the enzyme according to the invention.

| Amino group donors | Amino group acceptors | |
|---|---|---|
| | α-Ketoglutaric acid | α-Ketoadipic acid |
| D-alanine | +++ | ++ |
| D-α-aminoadipic acid | +++ | |
| D-aspartic acid | +++ | +++ |
| D-glutamic acid | | ++ |
| D-leucine | ++ | + |
| D-lysine | + | — |
| D-methionine | + | ++ |
| D-phenylalanine | + | (+) |
| D-proline | (+) | (+) |
| D-serine | ++ | + |
| D-tryptophan | + | + |
| D-tyrosine | + | — |
| D-valine | + | — |
| D-cystine | + | (+) |
| D-Ala—D-Ala | + | — |

+++ very good conversion
++ good conversion
+ significant conversion
(+) weak conversion
— no conversion Pyruvate, oxaloacetate and phenylpyruvate can also be employed as amino group acceptors.

What we claim is:

1. A D-aminoacid transaminase from Bacillus licheniformis ATCC 9945, which converts Cephalosporin C with an α-keto acid into α-ketoadipinyl-7-amino-cephalosporinic acid and the corresponding D-α-amino acid.

2. A process for the preparation of a D-aminoacid transaminase, which comprises
   (a) fermenting Bacillus licheniformis ATCC 9945 under aerobic conditions,
   (b) separating off the biomass from the fermentation medium and rupturing the cells and
   (c) isolating the fraction which converts cephalosporin C with an α-keto acid into α-ketoadipinyl-7-amino-cephalosporinic acid.

3. A D-aminoacid transaminase obtained by fermentation of Bacillus licheniformis ATCC 9945, removal and disruption of the cells and isolation of the fraction which converts CPC with an α-keto acid into α-ketoadipinyl-7-ACA.

* * * * *